(12) United States Patent
Sharkey et al.

(10) Patent No.: US 6,695,839 B2
(45) Date of Patent: Feb. 24, 2004

(54) METHOD AND APPARATUS FOR TREATMENT OF DISRUPTED ARTICULAR CARTILAGE

(75) Inventors: Hugh R. Sharkey, Menlo Park, CA (US); Gary S. Fanton, Portola Valley, CA (US)

(73) Assignee: Oratec Interventions, Inc., Menlo Park, CA (US)

( * ) Notice: Subject to any disclaimer, the term of this patent is extended or adjusted under 35 U.S.C. 154(b) by 0 days.

(21) Appl. No.: 09/780,648

(22) Filed: Feb. 8, 2001

(65) Prior Publication Data

US 2002/0107516 A1 Aug. 8, 2002

(51) Int. Cl.[7] .............................................. A61B 18/18
(52) U.S. Cl. .............................. 606/49; 606/41; 606/46; 606/48; 606/50; 607/105; 607/113
(58) Field of Search ............................. 606/41, 42, 46, 606/47, 48, 49, 50; 607/96, 104, 105, 113

(56) References Cited

U.S. PATENT DOCUMENTS

| 164,184 A | 6/1875 | Kidder |
|---|---|---|
| 300,155 A | 6/1884 | Starr |
| 371,664 A | 10/1887 | Brannan et al. |
| 452,220 A | 5/1891 | Gunning |
| 1,314,855 A | 9/1919 | Carpenter |
| 1,366,756 A | 1/1921 | Wappler |
| 1,731,627 A | 10/1929 | Johnson et al. |
| 1,735,271 A | 11/1929 | Groff |
| 1,814,791 A | 7/1931 | Ende |
| 1,908,583 A | 5/1933 | Wappler |
| 1,916,722 A | 7/1933 | Ende |
| 1,932,258 A | 10/1933 | Wappler |
| 1,943,543 A | 1/1934 | McFadden |
| 1,983,669 A | 12/1934 | Kimble |
| 2,002,594 A | 5/1935 | Wappler et al. |
| 2,004,559 A | 6/1935 | Wappler et al. |
| 2,050,904 A | 8/1936 | Trice |
| 2,056,377 A | 10/1936 | Wappler |

(List continued on next page.)

FOREIGN PATENT DOCUMENTS

| DE | 3511107 A1 | 10/1986 |
|---|---|---|
| DE | 3632197 A1 | 3/1988 |
| EP | 0 257 116 A1 | 3/1988 |

(List continued on next page.)

OTHER PUBLICATIONS

Attachment I: Competitive Literature on Generators with Bipolar Capabilities, IME Co., Ltd., pp. 60–86.

Attachment II: Competitive Literature on Bipolar Forceps and Footswitch Controls, IME Co., Ltd. pp. 87–104.

Auhull, Richard A., "The Use of the Resectoscope in Gynecology," Biomedical Business International. Oct. 11, 1990, pp. 91–93.

(List continued on next page.)

Primary Examiner—Rosiland K. Rollins
(74) Attorney, Agent, or Firm—Fish & Richardson P.C.

(57) ABSTRACT

An apparatus for treating disrupted articular cartilage comprising an elongate probe member having proximal and distal extremities and a handle coupled to the proximal extremity of the elongate probe member. The distal extremity has a peripheral wall defining a cavity and a distal opening communicating with the cavity. A controllable environment is created within the cavity when the distal extremity is placed substantially flush against the disrupted articular cartilage. An electrode is positioned within the cavity at a distance spaced inwardly of the distal opening. The disrupted articular cartilage is sealed to form a substantially continuous surface when energy is supplied to the electrode. A method of using the apparatus is provided.

5 Claims, 5 Drawing Sheets

U.S. PATENT DOCUMENTS

| | | |
|---|---|---|
| 2,090,923 A | 8/1937 | Wappler |
| 2,224,464 A | 12/1940 | Wolf |
| 2,275,167 A | 3/1942 | Bierman |
| 2,888,928 A | 6/1959 | Seiger |
| 3,152,590 A | 10/1964 | Zurdo et al. |
| 3,163,165 A | 12/1964 | Isikawa |
| 3,178,728 A | 4/1965 | Christensen |
| 3,460,539 A | 8/1969 | Anhalt, Sr. |
| 3,579,643 A | 5/1971 | Morgan |
| 3,595,239 A | 7/1971 | Petersen |
| 3,768,482 A | 10/1973 | Shaw |
| 3,776,230 A | 12/1973 | Neefe |
| 3,821,510 A | 6/1974 | Muncheryan |
| 3,828,780 A | 8/1974 | Morrison, Jr. |
| 3,856,015 A | 12/1974 | Iglesias |
| 3,867,728 A | 2/1975 | Substad et al. |
| 3,870,047 A | 3/1975 | Gonser |
| 3,879,767 A | 4/1975 | Substad |
| 3,886,600 A | 6/1975 | Kahn et al. |
| 3,901,242 A | 8/1975 | Storz |
| 3,902,494 A | 9/1975 | Haberlen et al. |
| 3,920,021 A | 11/1975 | Hiltebrandt |
| 3,920,022 A | 11/1975 | Pastor |
| 3,938,198 A | 2/1976 | Kahn et al. |
| 3,938,527 A | 2/1976 | Rioux et al. |
| 3,945,375 A | 3/1976 | Banko |
| 3,987,499 A | 10/1976 | Scharbach et al. |
| 3,987,795 A | 10/1976 | Morrison |
| 3,992,725 A | 11/1976 | Homsy |
| 4,043,342 A | 8/1977 | Morrison, Jr. |
| 4,074,718 A | 2/1978 | Morrison, Jr. |
| 4,085,466 A | 4/1978 | Goodfellow et al. |
| 4,129,470 A | 12/1978 | Homsy |
| 4,134,406 A | 1/1979 | Iglesias |
| 4,224,696 A | 9/1980 | Murray et al. |
| 4,224,697 A | 9/1980 | Murray et al. |
| 4,326,529 A | 4/1982 | Doss et al. |
| 4,344,193 A | 8/1982 | Kenny |
| 4,362,160 A | 12/1982 | Hiltebrandt |
| 4,375,220 A | 3/1983 | Matvias |
| 4,381,007 A | 4/1983 | Doss |
| 4,397,314 A | 8/1983 | Vaguine |
| 4,476,862 A | 10/1984 | Pao |
| 4,483,338 A | 11/1984 | Bloom et al. |
| 4,517,965 A | 5/1985 | Ellison |
| 4,517,975 A | 5/1985 | Garito et al. |
| 4,590,934 A | 5/1986 | Malis et al. |
| 4,593,691 A | 6/1986 | Lindstrom et al. |
| 4,597,379 A | 7/1986 | Kihn et al. |
| 4,601,705 A | 7/1986 | McCoy |
| 4,651,734 A | 3/1987 | Doss et al. |
| 4,811,733 A | 3/1989 | Borsanyi et al. |
| 4,815,462 A | 3/1989 | Clark |
| 4,838,859 A | 6/1989 | Strassmann |
| 4,873,976 A | 10/1989 | Schreiber |
| 4,894,063 A | 1/1990 | Nashef |
| 4,895,148 A | 1/1990 | Bays et al. |
| 4,907,585 A | 3/1990 | Schachar |
| 4,907,589 A | 3/1990 | Cosman |
| 4,924,865 A | 5/1990 | Bays et al. |
| 4,927,420 A | 5/1990 | Newkirk et al. |
| 4,944,727 A | 7/1990 | McCoy |
| 4,950,234 A | 8/1990 | Fujioka et al. |
| 4,955,882 A | 9/1990 | Hakky |
| 4,966,597 A | 10/1990 | Cosman |
| 4,976,709 A | 12/1990 | Sand |
| 4,976,715 A | 12/1990 | Bays et al. |
| 4,998,933 A | 3/1991 | Eggers et al. |
| 5,007,908 A | 4/1991 | Rydell |
| 5,009,656 A | 4/1991 | Reimels |
| 5,027,792 A | 7/1991 | Meyer |
| 5,085,657 A | 2/1992 | Ben-Simhon |
| 5,085,659 A | 2/1992 | Rydell |
| 5,098,430 A | 3/1992 | Fleenor |
| 5,100,402 A | 3/1992 | Fan |
| 5,103,804 A | 4/1992 | Abele et al. |
| 5,178,620 A | 1/1993 | Eggers et al. |
| 5,186,181 A | 2/1993 | Franconi et al. |
| 5,191,883 A | 3/1993 | Lennox et al. |
| 5,192,267 A | 3/1993 | Shapira et al. |
| 5,201,729 A | 4/1993 | Hertzmann et al. |
| 5,201,730 A | 4/1993 | Easley et al. |
| 5,201,731 A | 4/1993 | Hakky |
| 5,213,097 A | 5/1993 | Zeindler |
| 5,230,334 A | 7/1993 | Klopotek |
| 5,242,439 A | 9/1993 | Larsen et al. |
| 5,242,441 A | 9/1993 | Avitall |
| 5,261,906 A | 11/1993 | Pennino et al. |
| 5,267,994 A | 12/1993 | Gentelia et al. |
| 5,275,151 A | 1/1994 | Shockey et al. |
| 5,277,696 A | 1/1994 | Hagen |
| 5,281,218 A | 1/1994 | Imran |
| 5,284,479 A | 2/1994 | de Jong |
| 5,304,169 A | 4/1994 | Sand |
| 5,308,311 A | 5/1994 | Eggers et al. |
| 5,311,858 A | 5/1994 | Adair |
| 5,320,115 A | 6/1994 | Kenna |
| 5,323,778 A | 6/1994 | Kandarpa et al. |
| 5,334,193 A | 8/1994 | Nardella |
| 5,342,357 A | 8/1994 | Nardella |
| 5,348,554 A | 9/1994 | Imran et al. |
| 5,352,868 A | 10/1994 | Denen et al. |
| 5,354,331 A | 10/1994 | Schachar |
| 5,364,395 A | 11/1994 | West, Jr. |
| 5,366,443 A | 11/1994 | Eggers et al. |
| 5,366,490 A | 11/1994 | Edwards et al. |
| 5,382,247 A | 1/1995 | Cimino et al. |
| 5,397,304 A | 3/1995 | Truckai |
| 5,401,272 A | 3/1995 | Perkins |
| 5,409,481 A | 4/1995 | Poppas et al. |
| 5,415,633 A | 5/1995 | Lazarus et al. |
| 5,423,806 A | 6/1995 | Dale et al. |
| 5,428,699 A | 6/1995 | Pon |
| 5,433,739 A | 7/1995 | Sluijter et al. |
| 5,437,661 A | 8/1995 | Rieser |
| 5,437,662 A | 8/1995 | Nardella |
| 5,451,223 A | 9/1995 | Ben-Simhon |
| 5,458,596 A | 10/1995 | Lax et al. |
| 5,464,023 A | 11/1995 | Viera |
| 5,465,737 A | 11/1995 | Schachar |
| 5,484,403 A | 1/1996 | Yoakum et al. |
| 5,484,432 A | 1/1996 | Sand |
| 5,484,435 A | 1/1996 | Fleenor et al. |
| 5,486,170 A | 1/1996 | Winston et al. |
| 5,487,757 A | 1/1996 | Truckai et al. |
| 5,498,258 A | 3/1996 | Hakky et al. |
| 5,500,012 A | 3/1996 | Brucker et al. |
| 5,507,812 A | 4/1996 | Moore |
| 5,514,130 A | 5/1996 | Baker |
| 5,524,338 A | 6/1996 | Martyniuk et al. |
| 5,527,331 A | 6/1996 | Kresch et al. |
| 5,542,920 A | 8/1996 | Cheikh |
| 5,569,242 A | 10/1996 | Lax et al. |
| 5,599,346 A | 2/1997 | Edwards et al. |
| 5,630,839 A | 5/1997 | Corbett, III et al. |
| 5,643,255 A | 7/1997 | Organ |
| 5,681,282 A | 10/1997 | Eggers et al. |
| 5,683,366 A | 11/1997 | Eggers et al. |
| 5,688,270 A | 11/1997 | Yates et al. |
| 5,697,882 A | 12/1997 | Eggers et al. |
| 5,697,909 A | 12/1997 | Eggers et al. |

| | | |
|---|---|---|
| 5,718,702 A | 2/1998 | Edwards |
| 5,782,795 A | 7/1998 | Bays |
| 5,785,705 A | 7/1998 | Baker |
| 5,810,809 A | 9/1998 | Rydell |
| 5,814,040 A | 9/1998 | Nelson et al. |
| 5,843,078 A | 12/1998 | Sharkey |
| 6,068,628 A | 5/2000 | Fanton et al. |
| 6,135,999 A | 10/2000 | Fanton et al. |
| 6,149,620 A | 11/2000 | Baker et al. |
| 6,277,112 B1 * | 8/2001 | Underwood et al. ........ 604/114 |

FOREIGN PATENT DOCUMENTS

| | | |
|---|---|---|
| EP | 0 274 705 A1 | 7/1988 |
| EP | 0 479 482 A1 | 4/1992 |
| EP | 0 521 595 A2 | 1/1993 |
| EP | 0 542 412 A1 | 5/1993 |
| EP | 0 558 297 A2 | 9/1993 |
| EP | 0 566 450 A1 | 10/1993 |
| EP | 0 572 131 A1 | 12/1993 |
| EP | 0 682 910 A1 | 11/1995 |
| EP | 0 479 482 B1 | 5/1996 |
| EP | 0 729 730 A1 | 9/1996 |
| EP | 0 737 487 A2 | 10/1996 |
| EP | 0 783 903 A1 | 7/1997 |
| FR | 1122634 | 9/1956 |
| FR | 2 645 008 | 3/1989 |
| GB | 1 340 451 | 12/1973 |
| GB | 2160102 A | 12/1985 |
| GB | 2 164 473 A | 3/1986 |
| JP | 05-042166 | 5/1993 |
| SU | 637118 A | 12/1978 |
| WO | WO 85/02762 A1 | 7/1985 |
| WO | WO 92/10142 A1 | 6/1992 |
| WO | WO 93/01774 A1 | 2/1993 |
| WO | WO 93/16648 A1 | 9/1993 |
| WO | WO 93/20984 A1 | 10/1993 |
| WO | WO 95/01814 | 1/1995 |
| WO | WO 95/13113 A1 | 5/1995 |
| WO | WO 95/18575 A1 | 7/1995 |
| WO | WO 95/20360 A1 | 8/1995 |
| WO | WO 95/25471 A2 | 9/1995 |
| WO | WO 95/30373 A1 | 11/1995 |
| WO | WO 95/30377 A1 | 11/1995 |
| WO | WO 95/34259 A1 | 12/1995 |
| WO | WO 96/11638 A1 | 4/1996 |
| WO | WO 96/32051 A1 | 10/1996 |
| WO | WO 96/34568 A1 | 11/1996 |
| WO | WO 96/34571 A1 | 11/1996 |
| WO | WO 96/39914 A1 | 12/1996 |
| WO | WO 97/06855 A2 | 2/1997 |
| WO | WO 98/07468 A1 | 2/1998 |

OTHER PUBLICATIONS

Beadling, L., "Bi–Polar electrosurgical devices: Sculpting the future of arthroscopy", Orthopedics Today, vol. 17, No. 1, Jan. 1997, 4 pages.

Bosacco et al., "Functional Results of Percutaneous Laser Discectomy," The American Journal of Orthopedics, Dec. 1996, pp. 825–828.

Bromm et al., "Nerve Fibre Discharges, Cerebral Potentials and Sensations Induced by CO2 laser Stimulation", Human Neurobiology, vol. 3, (1984) pp. 33–40.

Buchelt et al., "Fluorescence Guided Excimer Laser Ablation of Intervertebral Discs In Vitro," Lasers in Surgery and Medicine, vol. 11, (1991) pp. 280–286.

Buchelt et al., "Erb:YAG and Hol:YAG Laser Ablation of Meniscus and Intervertebral Discs," Lasers in Surgery and Medicine, vol. 12 No. 4, (1992) pp. 375–381.

Choy et al., "Percutaneous Laser Disc Decompression: A New Therapeutic Modality", Spine, vol. 17 No. 8, (1992) pp. 949–956.

Christian, C. et al., "Allograft Anterior Cruciate Ligament Reconstruction with Patellar Tendon: An Endoscopic Technique", Operative Techniques in Sports Medicine, vol. 1, No. 1, Jan. 1993, pp. 50–57.

Cosman et al., "Theoretical Aspects of Radiofrequency lesions in the Dorsal Root Entry Zone," Neurosurgery, vol. 15 No. 6 (1984) pp. 945–950.

Cosset, J.M., Resistive Radiofrequency (Low Frequency) Interstitial Heating (RF Technique), Interstitial Hyperthermia, Dec. 6, 1993, pp. 2–5, 37.

Davis, "Early experience with Laser Disc Decompression", Florida M.A., 79(1) 37–39 (1992).

Ellman International Mfg., Inc., 1989, Catalog, pp. 1–15, 20.

Gehring W.J., "Exploring the Homeobox," Gene, 135, (1993), pp. 215–221.

Gerber et al., Der Orthopade: Offene Laserchirurgie am Bewegungsapparat, vol. 25, (1996) pp. 56–63.

Gottlob et al., "Holmium:YAG Laser Ablation of Human Intervertebral Disc: Preliminary Evaulation," Lasers in Surgery and Medicine, vol. 12, (1991) pp. 86–91.

Houpt, J. et al., "Experimental Study of Temperature Distributions and Thermal Transport During Radiofrequency Current Therapy of the Intervertebral Disc", Spine, vol. 21, No. 15, (1996), pp. 1808–1813.

Introduction to the LDD Disc Kit, Oct. 16, 1996.

Kelly L.E., "Purification and Properties of a 23kDa Ca2+–binding Protein," Biochem, J. (1990) 271, pp. 661–666.

Kolarik et al., "Photonucleolysis of Intervertebral Disc and it's Herniation," Research Institute of Higher Nervous Activity, vol. 51; (1990) pp. 69–71.

Leu et al., "Endoskopie der Wirbelsaule: Minimal–invasive Therapie," Der Orthopade, vol. 21, (1992) pp. 267–272.

Mayer et al., "Lasers in Percutaneous Disc Surgery: Beneficial Technology or Gimmick?," Acta Orthop Scand., vol 25 No. 251 (1993) pp. 38–44.

McCulloch et al., "Percutaneous Radiofrequency Lumbar Rhizolysis (rhizotomy)," DMA Journal, vol. 116, 30–32, Jan. 8, 1977.

Mehta et al., "The Treatment of Chronic back Pain: A Preliminary survey of the Effect of Radiofrequency Denervation of the Posterior Vertebral Joints", Anaesthesia, vol. 34 (1979) pp. 768–775.

Patil et al., "Percutaneous Disectomy Using the Electromagnetc Field Focusing Probe: A Feasability Study", Int. Surg., 76:30–32 (1991).

Phillips et al., "MR Imaging of Ho; YAG Laser Diskectomy with Histologic Correlation", JMRL, vol. 3 No. 3, May/Jun. 1993.

PRNewswire (Dec. 12, 1994), Two Physicians Perform First Outpatient Cervical Disc Procedure Using Laser Technology.

Quigley et al., "Laser Discectomy: Comparison of Systems", Spine, vol. 19 No. 3 (1994) pp. 319–322.

Savitz M.A., "Same–day Microsurgical Arthroscopic lateri-al–approach Laser–assisted (SMALL) Fluoroscopic Discectomy," J. Neurosurg., vol. 80, Jun. 1994 pp. 1039–1045.

Schatz et al., "Preliminary Experience With Percutaneous Laser Disc Decompression in the Treatment of Sciatica," CIS JCC, vol. 38, No. 5, Oct. 1995, pp. 432–436.

Sluijter et al., "Treatment of Chronic Back and Neck Pain by Percutaneous Therman Lesions," Persistant Pain: Modern Methods of Treatment, vol. 3, Sampson Lipton E.D. 141–179 (1981).

Sluijter, "The use of Radio Frequency Lesions For Pain Relief in Failed Back Patients," Int Disabil Studies vol. 10(1), Sep. 4, 1996, pp. 37–43.

Sluyter, "Radiofrequency Lesions in the Treatment of Cervical Pain Syndromes," Radionics, Inc. 2–24 (1989).

Sminia et al., "Effects of 434 MHz Microwave Hyperthermia applied to the rat in the region of the cervical Spinal Cord," Int. J. Hyperthermia, vol. 3(5): pp. 441–452 (1987).

Trimedyne, The Less Invasive Laser Advantage, Omni Spinal Introduction System.

Troussier, B. et al., "Percutaneous Intradiscal Radio–Frequency Thermocoagulation: A Cadaveric Study", Spine, vol. 30, No. 15, (Aug. 1995), pp. 1713–1718.

Vorwerck et al., "Laserablation des Nucleus Pulposus: Optische Eigenschaften von Degeneriertem Bandscheibengewebe in Wellenlangenberiech von 200 bis 2200nm", RöFo, vol. 151 No. 6, (1989) pp. 725–728.

Wilkins et al., Neurosurgery: Method of Making Nervous System Lesions, ch. 337, pp. 2490–2499.

Wolgin et al., "Excimer Ablation of Human Intervertebral Disc at 308 Nanometers", Lasers in Surgery and Medicine, vol. 9, (1989) pp. 124–131.

Yonezawa et al., "The System and Procedure of Percutaneous Intradiscal Laser Nucleotomy," Spine, vol. 15 No. 11 (1990).

* cited by examiner

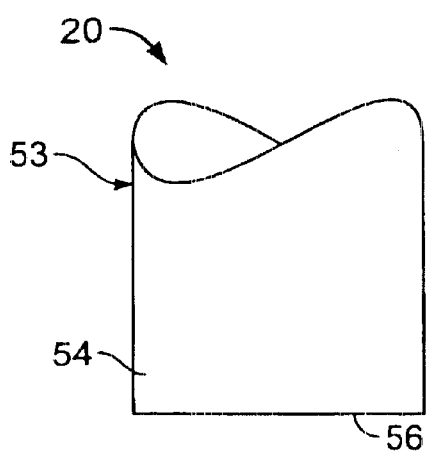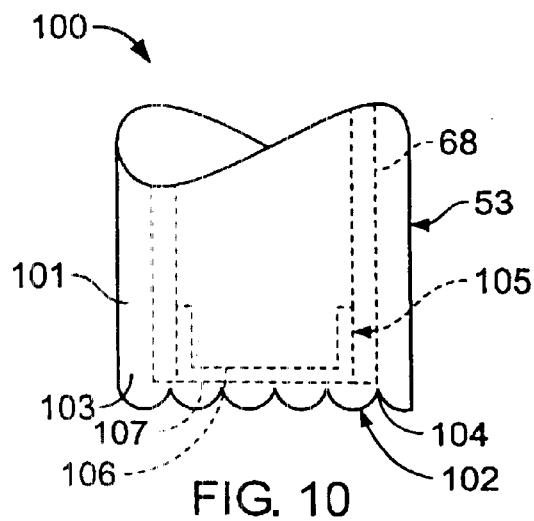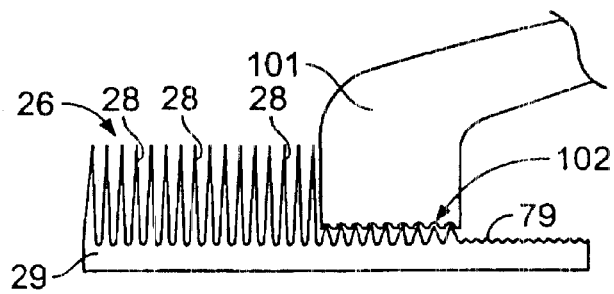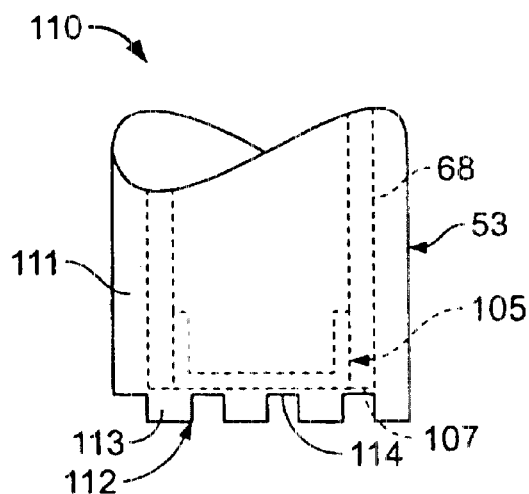

METHOD AND APPARATUS FOR TREATMENT OF DISRUPTED ARTICULAR CARTILAGE

BACKGROUND OF THE INVENTION

1. Field of the Invention

This invention relates generally to the use of electrosurgical methods and apparatuses for the treatment of damaged tissues and, more particularly, to the treatment of disrupted articular cartilage in the joint of a mammalian body.

2. Description of Related Art

The normal function of joints in humans depends on the distribution of relatively large forces across the body surfaces. In diarthrodial joints, the magnitude of the joint forces reaches levels four to seven times body weight. These forces are dispersed by articular cartilage in the joint. Proper cartilage function occurs via a highly organized extracellular matrix maintaining a fixed charge density and possessing a high affinity for water.

Chondromalacia occurs when cartilage beds in joints become worn and degenerate into strands of cartilage which extend away from their respective cartilage beds and into the joint cavity. The cartilage surface becomes visibly disrupted, fissured and fibrillated. The damaged cartilage has deleterious effects on the mechanical properties and normal function of articular surface. The fibrillated cartilage may break down and break off to form particulate matter. It is the particulate matter (broken fibrils) and various proteins and enzymes released when the normally smooth layered architecture of cartilage is undermined and frayed, which causes pain by irritating the synovial lining of the joint.

Treatment to date has included surgical intervention. In one arthroscopic procedure, a shaver is introduced through an arthroscope and is used to mechanically remove the strands of disrupted and fibrillated cartilage. However, this treatment can disrupt and remove part of the normal healthy cartilage bed and does not restore a smooth surface nor improve the mechanical function. Another modality for the repair and treatment of the damaged cartilage includes open procedures which can lead to increased recovery time and a possible increase in pain and further dysfunction of the joint.

Another exemplary device for treating fibrillated cartilage joint surfaces or irregular cartilage joint surfaces in an arthroscopic procedure delivers sufficient thermal energy to reduce the level of fibrillation of the cartilage joint surface. See U.S. Pat. No. 6,068,628 to Fanton et al. Particular care is used to minimize any undesired thermal effect on non-targeted tissue and thereby prevent necrosis below the surface of the cartilage joint surface into the healthy layer since cartilage does not grow and regenerate after being damaged. In view of the foregoing, it would be desirable to provide a thermal treatment device to coagulate the fibrillated cartilage strands together and closely monitor the ambient temperature in the immediate or surgical environment of the fibrillated cartilage so as to minimize undesirable cartilage damage and necrosis of underlying subchondral bone.

SUMMARY OF THE INVENTION

An apparatus for treating disrupted articular cartilage comprising an elongate probe member having proximal and distal extremities and a handle coupled to the proximal extremity of the elongate probe member is provided. The distal extremity has a peripheral wall defining a cavity and a distal opening communicating with the cavity. A controllable environment is created within the cavity when the distal extremity is placed substantially flush against the disrupted articular cartilage. An electrode is positioned within the cavity at a distance spaced inwardly of the distal opening. The disrupted articular cartilage is sealed to form a substantially continuous surface when energy is supplied to the electrode. A method of using the apparatus is provided.

In general, one advantage of the present invention is to provide a minimally invasive apparatus for delivering energy within a controllable environment to articular cartilage and particularly fibrillated articular cartilage, for treatment thereof, while minimizing collateral thermal effect on non-targeted tissue.

A further advantage of the present invention is to provide an electrosurgical probe which can more accurately monitor temperature of articular cartilage being treated within a controllable environment for a more precise feedback control of thermal energy delivered to tissue.

Another advantage of the present invention is to provide an apparatus of the above character in which sufficient thermal energy can be delivered to coagulate cartilage fibrils in predictable and reproducible levels thereby minimizing collateral damage.

Yet another advantage of the present invention is to provide an apparatus of the above character which can be used for treating chondromalacia and other articular cartilage defects.

The accompanying drawings, which are incorporated in, and form a part of this specification, illustrate embodiments of the invention and, together with the following description, serve to explain the principles of the invention.

BRIEF DESCRIPTION OF THE DRAWINGS

FIG. 9 is a schematic side elevational view of the end of the apparatus shown in FIG. 4.

FIG. 10 is a schematic side elevational view, similar to FIG. 9, of an end of another embodiment of the apparatus for treatment of fibrillated tissue of the present invention.

FIG. 11 is an enlarged perspective view of the end of the apparatus of FIG. 10 treating a section of fibrillated tissue.

FIG. 12 is a schematic side elevational view, similar to FIG. 9, of an end of yet another embodiment of the apparatus for treatment of fibrillated tissue of the present invention.

DESCRIPTION OF THE PREFERRED EMBODIMENTS

Reference will now be made in detail to the preferred embodiments of the invention, examples of which are illustrated in the accompanying drawings. While the invention will be described in conjunction with the preferred embodiments, it will be understood that they are not intended to limit the invention to those embodiments. On the contrary, the invention is intended to cover alternatives, modifications and equivalents, which may be included within the spirit and scope of the invention as defined by the appended claims.

Figure 1:
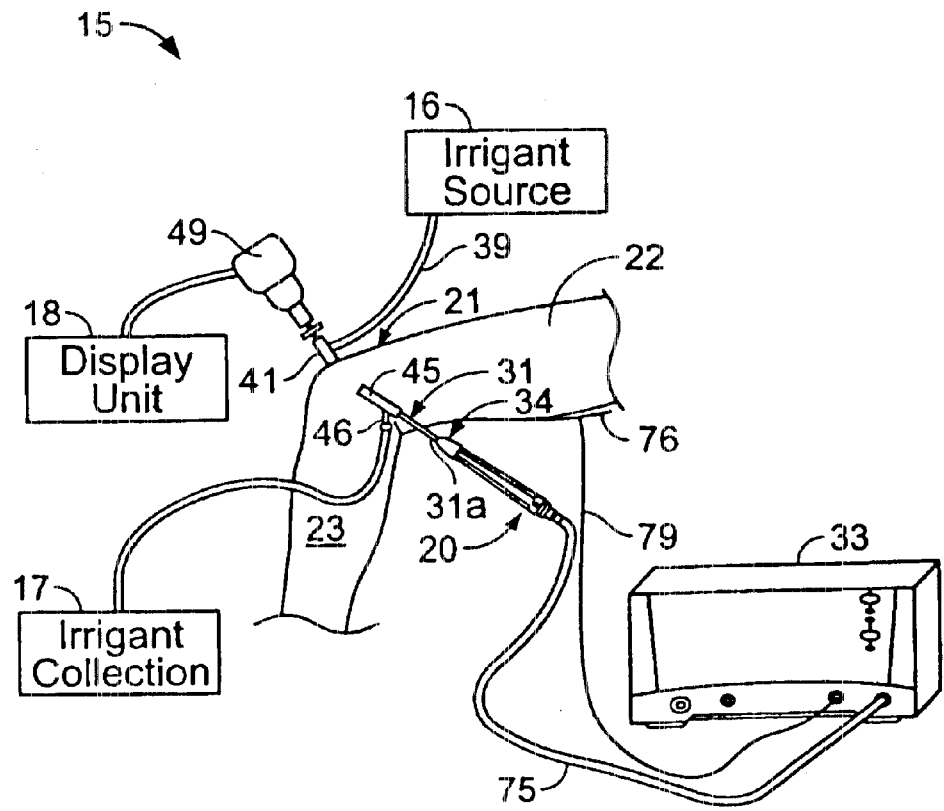
FIG. 1 is a schematic view of a system incorporating an apparatus for treatment of fibrillated tissue in use on a knee of a human body.
Figure 2:
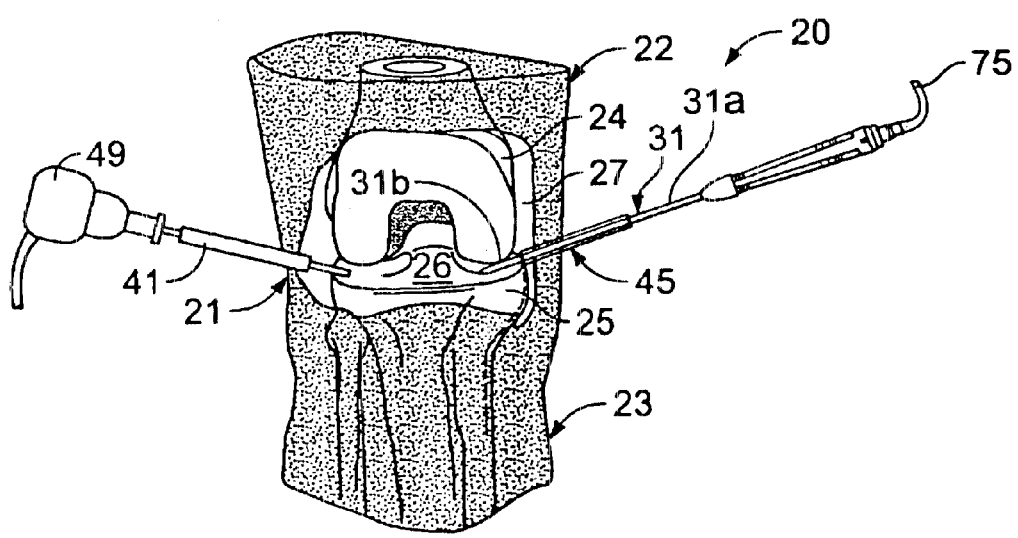
FIG. 2 is an enlarged schematic view of a knee capsule being treated by the system shown in FIG. 1.

Turning now to the drawings, wherein like components are designated by like reference numerals throughout the various figures, attention is directed to FIGS. 1 and 2 which illustrate a system 15 incorporating an irrigant source 16, an irrigant collection 17, a cathode ray tube or video display unit 18, and an apparatus 20 for treating a joint of a mammalian body. An exemplary knee joint 21 connecting thigh 22 and shin 23 is shown in FIGS. 1 and 2. Knee joint 21 is the junction of three bones, namely a thigh bone or femur 24, a shin bone or tibia 25, and a kneecap or patella (not shown). The ends of femur 24, tibia 25, and the patella are covered with articular cartilage 26 and are located within a joint capsule 27. Cartilage or cartilage fibrils 28 may extend from a respective cartilage bed 29 for a length of approximately one to ten millimeters and often extend approximately four to seven millimeters. Disrupted articular cartilage 26 can further include fissures 30 (see FIG. 3) and fragmented, avulsed or frayed cartilage. Hence, for purposes of the disclosure, disrupted articular cartilage 26 is broad enough to include cartilage that is fibrillated, fragmented and/or fissured.

Referring to FIGS. 1 and 2, apparatus 20 generally includes an elongate probe member 31 having a proximal extremity 31a and a distal extremity 31b and an energy source 33. A probe handle 34 is mounted to proximal extremity 31a and an active electrode 36 (shown in FIGS. 3 and 4) is provided on distal extremity 31b.

The apparatus of the present invention is preferably used in combination with other standard arthroscopic implements such as an irrigating system, a viewing system and a positioning system in addition to the otherwise conventional equipment utilized in a minimally invasive procedure conducted on a mammal under general anesthesia. For example, a standard arthroscopic system such as the one described in U.S. Pat. No. 6,068,628, the entire contents of which are incorporated herein by this reference, is preferably utilized for access to joint capsule 27. The irrigating system includes irrigant source 16 and irrigant collection 17. Any suitable irrigant source can be utilized, such as solution bags (not shown) of normal or isotonic saline.

An irrigating connection tube 39 includes tubing clamps or other suitable means for mechanically inhibiting and controlling the flow of the irrigating solution. A first percutaneous cannula 41 provides a portal for introducing irrigant into joint capsule 27 adjacent articular cartilage 26, as illustrated in FIGS. 1 and 2. A second cannula 45 provides a second portal or outflow port allowing irrigating fluid to exit joint capsule 27. Cannula 45 optionally includes a diversion tube 46 to direct the outflow of the irrigant away from an operator. One should appreciate that the irrigating system optionally may include a pump system that senses intra-articular pressure and maintains a desired pressure within joint capsule 27 to insure distraction of the joint and adequate hemostasis. Alternatively, intra-articular pressure can be generated in a well known manner by elevating the solution bags above the level of the patient making use of a simple gravity supply.

Either one or both of cannulas 41 and 45 may be incorporated into a cannula system allowing the introduction of an arthroscopic scope 49 for viewing the interior of joint capsule 27 and distal extremity 31b of probe member 31, as well as other interventional tools including other probes, cutting tools, electrosurgical instruments and electrothermal instruments which may be introduced into joint capsule 27. Arthroscopic scope 49 generally includes an optical rod lens which optionally is operably connected to a video camera that provides a video signal to a suitable display unit 18, such as a cathode ray tube, a liquid crystal display or a plasma monitor, for viewing by the operator.

Figure 3:
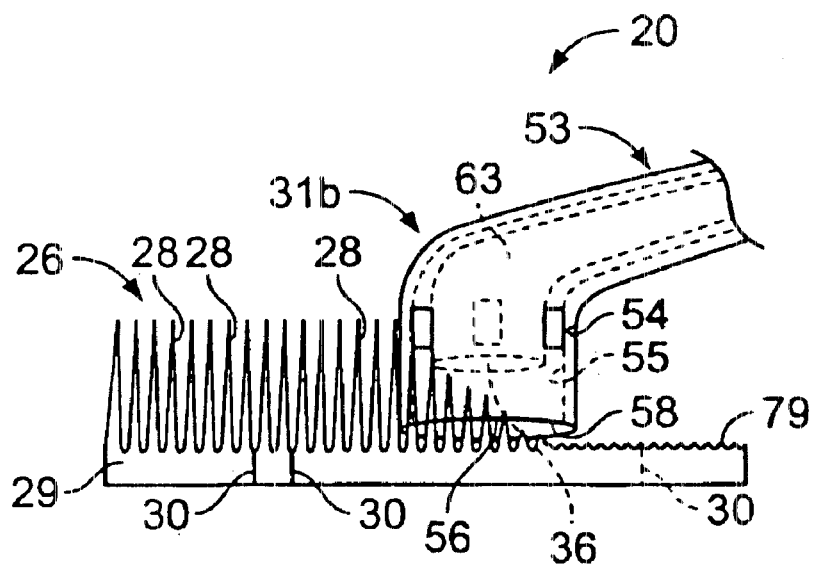
FIG. 3 is an enlarged perspective view of an end of the apparatus shown in FIG. 1 treating a section of fibrillated tissue.
Figure 4:
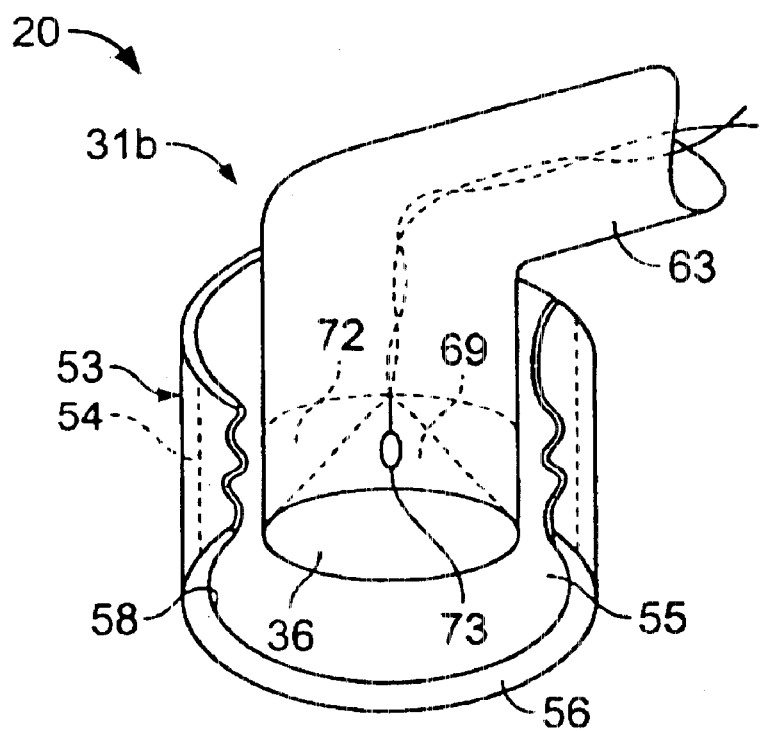
FIG. 4 is an enlarged perspective view, partially cut away of the end of the apparatus shown in FIG. 3.
Figure 5:
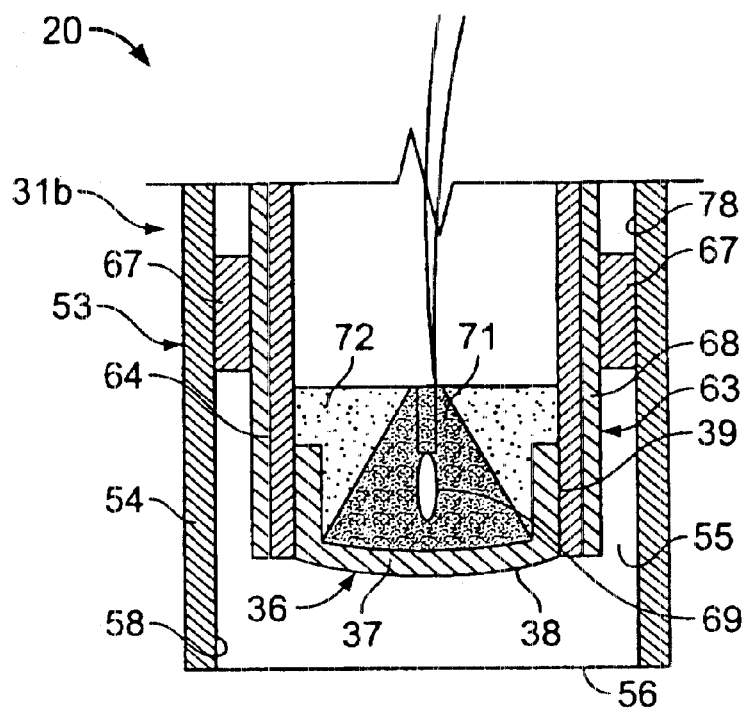
FIG. 5 is a cross-sectional view of the apparatus shown in FIG. 4 taken along line 5—5 of FIG. 4.

Probe member 31 includes an elongated and hollow outer shaft 53, as shown in FIGS. 3–5. A peripheral wall 54 is formed by a distal extremity of outer shaft 53. Peripheral wall 54 defines a cavity 55. A lower edge 56 of peripheral wall 54 defines a distal opening 58 communicating with cavity 55. Although the illustrated peripheral wall 54 is tubular, one should appreciate that it may take other forms. For example, the peripheral wall may be oval or polygonal in shape.

Active electrode 36 is made from any suitable conductive material such as stainless steel, platinum, iridium, titanium, silver and their alloys or any other medical grade metal. The electrode 36 is cup-shaped, as shown in profile in FIG. 5, and has a distally-oriented end wall 37 provided with an outer or distal surface 38 and a tubular side wall 39 extending proximally from the distal opening 58. Outer surface 38 is shown as being convex with an outwardly bowed shape. It should be appreciated, however, that the outer surface 38 of electrode end wall 37 can be planar or of any other suitable shape and be within the scope of the present invention.

Figure 6:
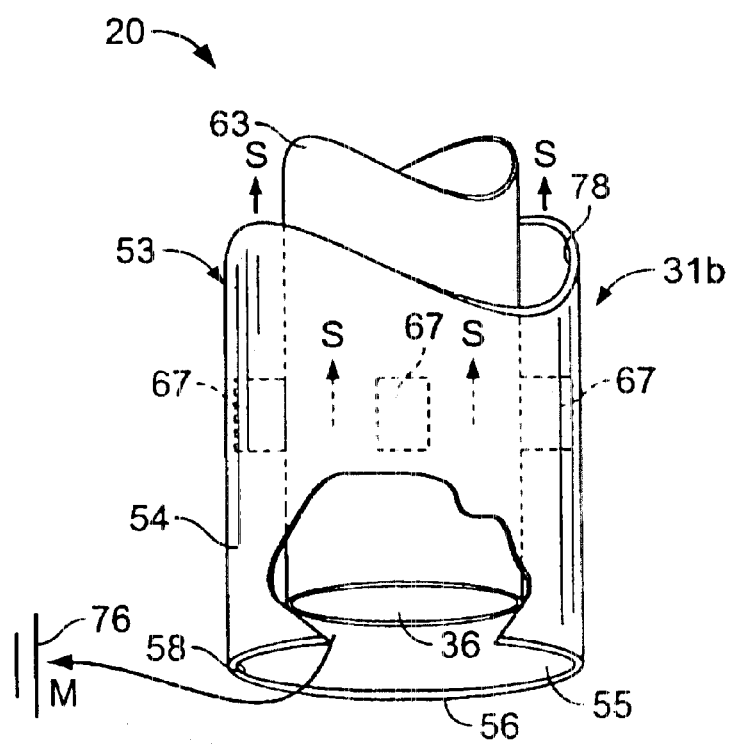
FIG. 6 is a perspective view, partially cut away of the apparatus shown in FIG. 4, illustrating an energy current pathway therefor.

Distal extremity 31b of probe member 31 includes an inner shaft 63 which is affixed to outer shaft 53 by a plurality of brackets or spacers 67, as shown in FIGS. 5 and 6. Conductive lead means is included with inner shaft 63 for providing energy to active electrode 36. Such conductive lead means can be in the form of a tubular member or tube 64 made from any suitable conductive material and preferably a suitable medical grade conductor such as stainless steel 304 or any other stainless steel, MP35N, alloy metals, noble metals, any other suitable conductive carbon material or imbedded plastics or polymers. The distal end of tube 64 is secured to active electrode 36 by any suitable means and, as shown, the tube 64 is press fit about the circumferentially-extending side wall 39 of the active electrode so as to be electrically coupled to the active electrode. An additional tubular member or outer side wall, preferably in the form of a sleeve 68, is shrunk about or otherwise suitably disposed around the outside of tube 64 and thus side wall 39 of the active electrode 36. Sleeve 68, which is preferably formed from a thermally-insulating material and is more preferably formed from teflon (PTFE), polyolefin or nylon (PFA) or other plastics or polymers, serves to thermally insulate electrode side wall 39 and conductive tube 64 disposed thereabout.

Inner shaft 63 and active electrode 36 carried thereby are supported within peripheral wall 54 by the one or more spacers 67. More specifically, spacers 67 are circumferentially disposed about the inner shaft 63 and serve to space active electrode 36 and the inner shaft 63 radially within outer shaft 53. The spacers 67 can be made from any suitable material such as glass, ceramic or any nonconductive electrical and/or thermal material. Active electrode 36 is spaced inwardly or proximally from opening 58a distance of approximately two to ten millimeters and preferably approximately two to five millimeters so as to be recessed within distal extremity 31b.

A temperature or heat sensor 69 is preferentially carried by distal extremity and preferably by inner shaft 63 for measuring and monitoring the temperature of active electrode 36 within cavity 55. Heat sensor 69 is of a conventional design and may consist of a thermocouple, a thermistor, a resistive wire, an integrated circuit (IC) or any other suitable sensor. The sensor 69 is electrically coupled to active electrode 36. In this regard, a heat sink 71 is disposed within the proximal recess formed by end wall 37 and side wall 39 of electrode 36. The heat sink is made from any suitable thermally-conductive material such as a heat sink paste and is secured to the proximal surface of end wall 37. Sensor 69 is encapsulated by heat sink 71 and located in close proximity to electrode end wall 37. The heat sink 71 is not in contact with side wall 39 and is preferably spaced radially inwardly from the side wall 39. Although the heat sink can be of any suitable shape, it is preferably conical in shape so as to ensure contact with the entire proximal surface of end wall 37 and yet remain separated from side wall 39. An optional insulator 72 made from any suitable thermally insulating material is disposed between heat sink 71 and side wall 39 for further minimizing any effect on temperature sensor 69 from the side wall.

System 15 of the present invention is an electrothermal system which includes probe apparatus 20 and energy source 33 to thermally coagulate disrupted articular cartilage, for example a fibrillated articular surface typically present in Grades I, II and III chondromalacia. Energy source 33 is preferably a radiofrequency generator and controller hereinafter referred to as radiofrequency generator 33. Radiofrequency generator 33 includes a feedback controller which is dependent upon temperature and/or impedance. Active electrode 36 is electrically connected to radiofrequency generator 33 by means of conductive tube 64 and a suitable connecting cable 75, which extends from the energy source 33 to probe handle 34 to electrically couple to the proximal end of tube 64. As shown in FIG. 1, connecting cable 75 may be integrated to the probe handle 34 to form a one-piece unit between apparatus 20 and probe handle 34. This provides a fluid resistant environment within electrosurgical probe handle 34 to prevent electrical disconnects and shorting between apparatus 20 and energy source 33. It will also be appreciated that probe handle 34 and connecting cable 75 may also be separate units utilizing a keyed and/or electrically insulated connection at a proximal end of probe handle 34.

In one embodiment, a grounding pad 76 is provided on thigh 22 of the patient's body as shown in FIG. 1. The grounding pad 76 may also be placed on any electrically suitable location of the body to complete the circuit. Grounding pad 76 is electrically connected to radio frequency generator 33 via a second return connecting cable 77 to complete the electrical circuit. Radiofrequency generator 33 can deliver high frequency (RF) voltage in the range of one to 350 watts.

Optionally, impedance is monitored by energy source 33 along the electrical circuit between power output and return input of the energy source 33. The energy source 33 monitors the impedance of the electrical circuit by measuring the difference between the output power and the input return as a function of voltage over current. In a typical monopolar system the impedance level is about 100 ohms and in a typical bipolar system the impedance level is about 60 ohms.

The feedback controller of radiofrequency generator 33 monitors the temperature of the tissue or cartilage being treated by monitoring the temperature experienced by sensor 69 located in the proximity of the active electrode. The feedback controller compares such temperature to a programmed temperature profile. The feedback control can also directly monitor system impedance of the electrical circuit. If the measured impedance exceeds a predetermined level, energy delivery to active electrode 36 is disabled or adjusted thus ceasing or adjusting delivery of thermal energy to active electrode 36. If the temperature within cavity 55 measured by sensor 69 exceeds a predetermined desired temperature, energy delivery to active electrode 36 is disabled or adjusted thus ceasing or adjusting delivery of thermal energy to active electrode 36 and thereby controlling the temperature within the microenvironment created by cavity 55.

Optionally, apparatus 20 may be used in combination with a suction source. For example, the probe member includes a lumen 78, as shown in FIGS. 4–6, which extends from cavity 55 towards proximal extremity 31a (not shown in FIGS. 4–6) of the probe member and through probe handle 34. In the illustrated embodiment, lumen 78 is annular in cross section at distal extremity 31b where the lumen communicates with cavity 55. Specifically, such annular lumen 78 is formed at its outside by peripheral wall 54 and at its inside by inner shaft 63. Lumen 78 fluidly connects with the suction source via a suitable fluid coupling adjacent proximal extremity 31a in a conventional manner. In such configuration, the suction source can be activated to produce a suction effect within lumen 78 and cavity 55, as is indicated by arrows S in FIG. 6. The suction source can be activated by a physician to aspirate the joint cavity as desired by the physician. When the suction source is activated, fluid, particulates and other matter within the surgical field are aspirated into a collection vessel. One should appreciate, however, that apparatus 20 may be used with or without a suction source.

In operation and use, a suitable positioning system can be used to immobilize joint 25 to facilitate the operator's or physician's access to joint capsule 27. The positioning system is selected based upon the specific anatomy to be addressed with the procedure in accordance with the present invention.

After the patient has been appropriately sedated or anesthetized, joint capsule 27 is pressurized by a suitable irrigant to create a work area within the joint space 27, as shown in FIG. 2. For example, fluid inflow from irrigant source 21 by means of pump and/or gravity introduces pressurized irrigant fluid into joint capsule 27 so as to create a workspace within joint capsule 27 and provide a flushing and cooling action. The irrigating solutions are commonly stored in the operating room and are then used at room temperature. The saline or other irrigating fluid from irrigant source 21 further serves to cool cartilage bed 29 outside of the treatment zone defined by cavity 55. Such cooling minimizes the thermal heating of the deeper layers of cartilage bed 29 and thus inhibits the undesirable thermal damage of such deeper tissues.

Probe handle 34 is grasped by the physician to introduce distal extremity 31b of probe member 31 through cannula 45 and into the joint capsule of the patient and thereafter to position lower edge 56 of distal extremity 31b substantially flush against the disrupted articular cartilage 26. Scope 49 allows the physician to view distal extremity 31b within joint capsule 27 and thus facilitates movement of distal extremity relative to articular cartilage bed 29 by the physician. In particular, the physician can manipulate probe member 31 such that opening 58 is substantially flush against disrupted articular cartilage 26 as shown in FIG. 3. A controllable environment, that is an environment or area separate from the remainder of joint capsule 27 outside of cavity 55, is created within cavity 55 when lower edge 56 is placed substantially flush against disrupted articular cartilage 26.

Probe member 31 temporarily confines a volume of fluid and the disrupted articular cartilage 26 within the controllable environment of cavity 55 as distal extremity 31a is swept across the surface of articular cartilage bed 29. The physician activates radiofrequency generator 33 and radio frequency energy is supplied to the controllable fluid-filled environment within cavity 55. The saline and/or other conductive irrigants present within joint capsule 27 serve to transmit such radio frequency energy and, together with other tissue of the mammalian body, transmit the radio frequency energy to grounding pad 76. The resulting monopolar current path is shown schematically by arrow M in FIG. 6. The passing of such radio frequency through the fluid within cavity heats such fluid to a temperature that can be monitored by temperature sensor 69. The amount of energy supplied to electrode 36 controls the temperature of the electrode and the fluid within the environment of cavity 55.

The disrupted articular cartilage over which cavity 55 rests, for example the fibrillated articular cartilage fibrils or strands 28 extending from cartilage bed 29, are thermally treated by the heated fluid within cavity 55 so as to become coagulated cartilage. Fibrillated strands 28 which contact distal surface 38 of active electrode 36 are similarly coagulated or melded and thus treated. Subjecting the fibrillated articular cartilage strands 28 to temperatures in the range of approximately 50° C. to 100° C., and preferably in the range of approximately 55° C. to 85° C., causes the fibrillated articular cartilage strands 28 to meld into cartilage bed 29 and thus form a substantially smooth coagulated mass on the surface of the cartilage bed 29 as indicated by numeral 79 in FIG. 3. In this manner, the cartilage bed 29 is sealed into a coagulated mass 79. The treatment of disrupted articular cartilage 26 by apparatus 20 in the foregoing manner can also result in the sealing of fissures 30, one of such sealed fissures 30 being shown by a dashed line in FIG. 3, and the sealing of any fragmented, avulsed or otherwise disrupted cartilage into a coagulated mass 79.

Active electrode 36 is spaced or recessed inwardly from opening 58 so as to minimize direct contact between the active electrode and cartilage bed 29 when apparatus 20 is utilized for treating fibrillated articular cartilage strands 28. Active electrode 36 is recessed within opening 58a distance that allows for the targeted fibrillated articular cartilage strands 28 to extend into the cavity or space created by the extension of peripheral wall 54 beyond distal surface 38 of the active electrode. The distance between the active electrode and the surface of the articular cartilage bed 29 is preferably such that the delivery of energy from radiofrequency generator 33 coagulates the fibrillated articular cartilage strands into a coalesced and singular mass to form a contiguous articular cartilage surface. Such distance reduces the delivery of thermal energy to underlying subchondral bone thus preventing a vascular necrosis (AVN). The movement of apparatus 20 by the operating physician across the disrupted articular cartilage 26 limits the time of exposure of such cartilage to thermal heating, which is also a factor in preventing AVN.

As thermal energy is so delivered to active electrode 36, the physician advances or sweeps probe member 31 continuously across cartilage bed 29 at a speed that allows for sufficient coagulation of fibrillated articular cartilage strands 28 to occur and form a coagulated mass 79, as shown in FIG. 3, but without excessive thermal exposure to deeper viable tissues including cartilage bed 29 and subchondral bone such as tibia 25 (FIG. 2). The sweeping motion of the probe member along cartilage bed 29 results in a convective thermal effect that follows the path of the probe.

One should appreciate that tissues do not immediately heat up when exposed to thermal energy. The exposure time of thermal energy upon an area of cartilage bed 29 is a factor in treatment effectiveness. The phenomena known as thermal latency of tissues determines the thermal response time, or thermal conduction time of the targeted tissue being treated. The apparatus of the present invention is particularly suited for providing locally high temperatures confined to a small area or controllable environment that is moveable across the surface of the fibrillated cartilage. Peripheral wall 54 substantially isolates the targeted tissue, that is the fibrillated cartilage extending into cavity 55, from adjacent non-targeted tissue, in this case all tissue located outside peripheral wall 54. Accordingly, the apparatus of the present invention can be employed to coagulate tissues safely within this controllable thermal environment while minimizing the thermal exposure of adjacent tissue. By creating a controllable thermal environment within the confines of cavity 55, the physician can progressively coagulate an entire degenerative area of fibrillated cartilage regardless of a particular patients' individual pathology and characteristics. Because the thermal energy is confined to a select area within the electrosurgical probe at any moment in time, that is the area confined the outline of peripheral wall 54 and exposed to cavity 55, unwanted damage and effect to other non-targeted tissue is minimized and/or prevented.

One should also appreciate that peripheral wall 54 substantially isolates the targeted tissue from the flushing and cooling action, as discussed above, of the saline and other irrigants within joint capsule 27. In this regard, peripheral wall 54 defines a controllable environment within cavity 55 which minimizes the flow of ambient cooling and irrigating fluids past active electrode 36 and cartilage tissue within cavity 55 and thus inhibits convective cooling of the active electrode 36 and such tissues and undesired temperature fluctuations in the treatment area. The controllable environment defined by peripheral wall 54 further serves to minimize the risk of contact between the active electrode and nearby anatomical structures, thus also minimizing unwanted temperature fluctuations in the treatment area and preventing non-targeted tissue damage. The confined and controllable thermal environment, substantially free from the flushing and cooling actions within joint capsule 27, also permits more accurate temperature measurement for the feedback control in radiofrequency generator 33 such that a precise energy delivery may be effected.

In the event that apparatus 20 is used in combination with a suction source, insulating sleeve 68 insulates active electrode 36 from convective cooling of the saline and other irrigating fluids which flow through lumen 78 during irrigation of cavity 55. Advantageously, insulating sleeve 68 further minimizes temperature fluctuations in the treatment area because sleeve 68 minimizes convective cooling of active electrode 36.

Temperature sensor 69 located within cavity 55 permits the ambient temperature of the controlled environment to be accurately monitored. Insulating sleeve 68 inhibits convective cooling of active electrode 36 from fluid traveling through suction lumen 78 when apparatus 30 is used in combination with a suction source. Accordingly, the temperature of electrode 36 and the fluid within cavity 55 can be accurately monitored and regulated thereby minimizing the possibility of thermal damage to non-targeted tissue as well as to apparatus 20. For example, because the temperature within cavity 55 is accurately monitored, predictable and reproducible levels of energy can be delivered in order to effectively meld fibrillated articular cartilage strands 28 and minimize collateral thermal effect on non-targeted tissue including underlying cartilage bed 29 and subchondral bone 25. The coupling of sensor 69 only to end wall 37 of active electrode 36, and not side wall 39 thereof, further ensures accurate temperature measurements by sensor 69. The utilization of insulator 72 is also beneficial in this regard.

The disposition of electrode 36 inhibits damage to probe member 31. As is known in the art, arching and sparking may occur in the event that an electrode contacts metal surfaces, for example, cannulas within surgical environments. Because active electrode 36 of the present invention is located within peripheral wall 54 and cavity 55a distance from opening 58, contact of the active electrode 36 with other items within joint capsule 27, as well as the resulting arching and sparks, are minimized and/or prevented. The configuration of the present invention thus protects scope 49, cannulas 41, 45 and other instruments present in the joint capsule because direct contact of such items with active electrode 36 is prevented.

The structure of the apparatus and probe member may vary widely and fall within the scope of the present invention. For example, the active electrode may have a variety of different geometric configurations. Although active electrode 36 is shown as being convex in FIG. 5, one should appreciate that other geometries may be used. For example, the electrode may be spherical, flat, asymmetric or concave. In addition, it should be appreciated that the energy source, apparatus and method of the present invention can utilize other suitable frequencies along the electromagnetic spectrum, including infrared, coherent light, sonic and microwave, for heating the controllable environment created by cavity 55 and the disrupted articular cartilage 26 exposed thereto and be within the scope of the present invention.

Figure 7:
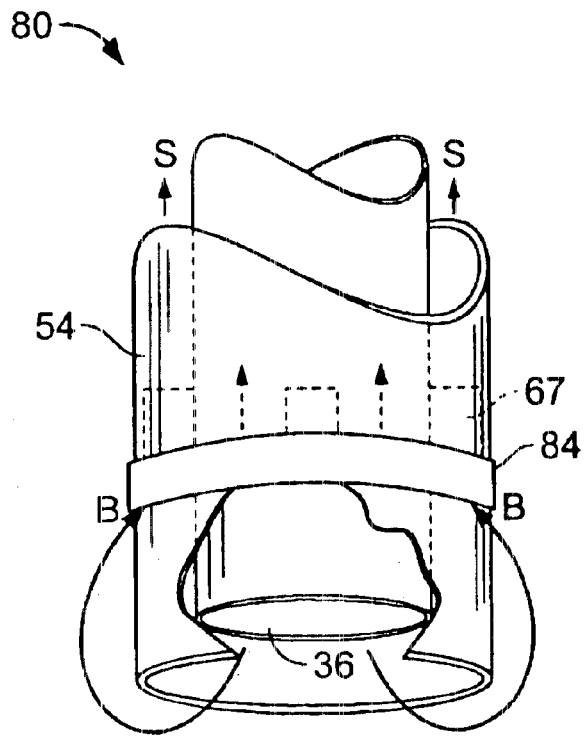
FIG. 7 is a perspective view, partially cut away and similar to FIG. 6, illustrating an energy current pathway of a further embodiment of the apparatus for treatment of fibrillated tissue of the present invention.

In another embodiment, as shown in FIG. 7, apparatus 80 therein is substantially similar to apparatus 20 and like reference numerals have been used to describe like components of the various embodiments. Apparatus 80 is bipolar and includes an annular external return electrode 84 provided on an external surface of peripheral wall 54 for permitting the energy source to operate in a sesquipolar mode. Return electrode 84 is electrically connected to the radiofrequency generator 33 and completes the electrical circuit therewith instead of a grounding pad. The bipolar current path extending from active electrode 36 to return electrode 84 is shown schematically in FIG. 7 by arrow B. Although return electrode 84 is shown having a tubular or cylindrical configuration in FIG. 7, one should appreciate that other geometries may be used. For example, the return electrode may be conical or toroidal in shape, segmented, or be located on just one side of peripheral wall 54 and still fall within the scope of the present invention. In use and operation, apparatus 80 is used in the same manner as apparatus 30 except that a grounding pad on the patient's body is not necessary to complete the electrical circuit and is thus not used.

Figure 8:
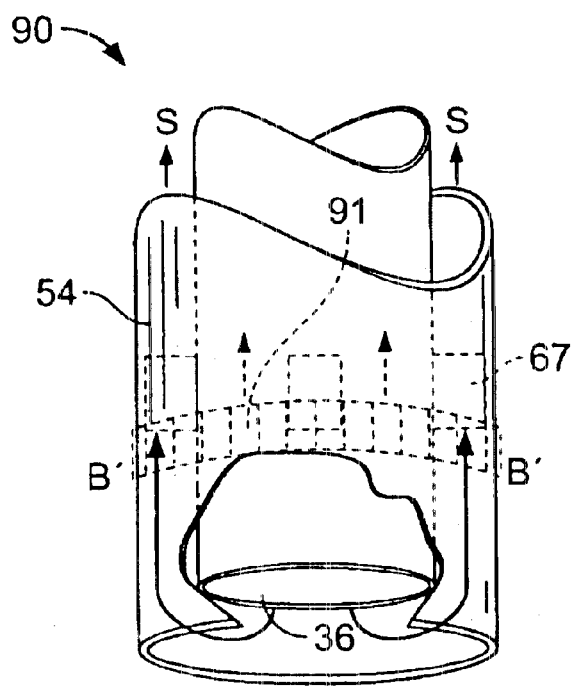
FIG. 8 is a perspective view, similar to FIG. 6, illustrating an energy current pathway of a further embodiment of the apparatus for treatment of fibrillated tissue of the present invention.

In another embodiment, shown in FIG. 8, apparatus 90 therein is bipolar and includes an internal return electrode 91 provided on an internal surface of peripheral wall 54. Similar to apparatus 80, internal return electrode 91 of apparatus 90 is electrically connected to the radiofrequency generator 33 and competes the electrical circuit therewith instead of a grounding pad. The bipolar current path extending from active electrode 36 to return electrode 91 is shown schematically in FIG. 8 by arrow B'. In use and operation, apparatus 90 is used in substantially the same manner as apparatus 80.

The geometry of the peripheral wall may also vary widely and fall within the scope of the present invention, as shown in FIGS. 9, 10, and 12. For example, peripheral wall 54 of apparatus 20 has a lower edge 56 that is substantially planar, as is shown in FIGS. 4–6 and 9. In another embodiment shown in FIGS. 10 and 11, apparatus 100 includes a tubular peripheral wall 101 having a lower edge 102 which is scalloped with a plurality of semicircular segments or scallops 103 separated by a plurality of respective recesses 104. Again it is noted that like reference numerals have been used to describe like components of the various embodiments. An electrode 105, substantially similar to electrode 36, is carried within outer shaft 53 and has an end wall 106 having an outer or distal surface 107 of any suitable shape and, as shown, is substantially planar (see FIG. 10). Distal surface 107 of the electrode 105 is spaced inwardly or proximally from the base of recesses 104a distance ranging from one to twelve millimeters and preferably approximately six millimeters.

The shape of lower edge 102 in FIG. 11 facilitates raking individual fibrillated articular cartilage strands 28 into the cavity as a physician sweeps the probe member of apparatus 100 along cartilage bed 29. In particular, the scalloped lower edge 102 inhibits matting of fibrillated cartilage as the probe member of apparatus 100 is swept along bed 29. This phenomena is similar to individual blades of grass returning to their substantially vertical position after a rake passes over them. In addition, the semicircular segments 103 groom the fibrillated cartilage and thus enhance the sealing effect of the lower edge against the cartilage strands 28, thereby minimizing undesirable convective inflow of the exterior irrigant into the controllable environment within cavity 55.

Yet another embodiment is shown in FIG. 12 in which apparatus 110 includes a peripheral wall 111 having a lower edge 112 which is scalloped with a plurality of stepped segments 113, each of which is shown as being rectangular in shape. Apparatus 110 has similarities to apparatus 20 and 100 and like reference numerals have been used to describe like components of apparatus 20, 100 and 110. Each pair of stepped segments is separated by a recess 114, which is also rectangular in shape. Distal surface 107 of the electrode 105 is spaced inwardly or proximally from the base of recesses 114a distance ranging from one to twelve millimeters and preferably approximately six millimeters.

The steps or tooth-like segments 113 advantageously seal the articular cartilage in a deep fibril environment, that is a dense field of cartilage strands 28, by allowing the fibrillated articular cartilage strands that are being advanced upon to enter the cavity or chamber in the distal extremity of apparatus 110. Convection is less of a concern in such a deep fibril environment because slots are filled by the entering fibrillated articular cartilage in the same manner as discussed above with respect to apparatus 100.

As can be seen from the foregoing, the present invention provides a minimally invasive apparatus for delivering energy to disrupted articular cartilage and particularly cartilage fibrils extending outwardly from a cartilage bed for treatment thereof while minimizing collateral thermal effect on non-targeted tissue. The present invention creates a controlled environment for the purpose of melding cartilage fibrils extending from the cartilage bed. The present invention delivers sufficient thermal energy to coagulate fibrillated articular cartilage to form a more normal and sealed articular cartilage surface in predictable and reproducible levels thereby minimizing collateral damage to nearby non-target and healthy tissue. The present invention can be used for treating chondromalacia and other articular cartilage defects.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the claims appended hereto and their equivalents.

What is claimed is:

1. A system for treating disrupted articular cartilage comprising:
    an elongate probe member having:
        proximal and distal portions, the distal portion having a peripheral will, the peripheral wall defining a cavity and having a distal opening communicating with the cavity, the peripheral wall being configured to create a controllable environment within the cavity when the distal opening is placed substantially flush against disrupted articular cartilage, and
        an electrode positioned within the cavity at a distance spaced inwardly of the distal opening of the peripheral wall;
    an energy source coupled to the electrode and configured to provide a supply of energy suitable for sealing disrupted articular cartilage to form a substantially continuous surface, and
    a temperature sensor within the distal portion for monitoring the ambient temperature within the controllable environment,
    wherein the electrode has a distally-oriented wall and a circumferentially-extending side wall extending proximally from the distal opening, the temperature sensor being distal behind the distally-oriented wall within a thermally-conductive fill material adhered to the distally-oriented wall for monitoring of the temperature of the distally-oriented wall.

2. The system of claim 1 wherein the thermally-conductive fill material is spaced inwardly from the side wall for enhancing accuracy in the monitoring of the temperature of the distally-oriented wall.

3. The system claim 2, further comprising an insulating material disposed between the thermally-conductive fill material and the side wall.

4. A system for treating a fluid-filled joint mammalian body having disrupted articular cartilage, the system comprising: (i) an elongate probe member having proximal and distal portions, the distal portion having a peripheral wall, the peripheral wall defining a cavity and having a distal opening communicating with the cavity, the peripheral wall being configured to create a controllable fluid-filled environment in the cavity when the distal opening is placed substantially flush against disrupted articular cartilage, and an electrode carried by the distal portion within the cavity in a position spaced inwardly of the distal opening, (ii) an energy source coupled to the electrode and configured to provide a supply of energy suitable for melding together the disrupted articular cartilage whim energy is provided to the electrode to heat the controllable fluid environment, and (iii) a temperature sensor carried by the distal portion within the cavity for monitoring ambient temperature within the controllable fluid-filled environment, wherein:
    the electrode is cup-shaped and has an end wall facing the distal opening and a side wall extending proximally from the distal opening,
    the electrode temperature sensor is disposed behind the end wall, and
    an outer side wall of a thermally insulating material surrounds the side wall of the electrode for enhancing accuracy in the monitoring of the ambient temperature.

5. The system of claim 4 wherein the elongate probe member defines a lumen extending longitudinally therethrough, the outer side wall being spaced inwardly from the peripheral wall for forming an annular opening for the lumen.

* * * * *

UNITED STATES PATENT AND TRADEMARK OFFICE
CERTIFICATE OF CORRECTION

PATENT NO. : 6,695,839 B2
DATED : February 24, 2004
INVENTOR(S) : Hugh R. Sharkey and Gary S. Fanton It is certified that error appears in the above-identified patent and that said Letters Patent is hereby corrected as shown below:

Title page,
Item [56], References Cited, U.S. PATENT DOCUMENTS, "4,074,718" reference, delete ", Jr."; "5,428,699" reference, delete "6/1995" and insert -- 7/1995 --; and "5,810,809" reference, delete "9/1998" and insert -- 8/1998 --.
FOREIGN PATENT DOCUMENTS, "WO 95/01814" reference, after "01814" insert -- A1 --.
OTHER PUBLICATIONS, "Auhull, Richard A." reference, delete "Auhull" and insert -- Auhll --; "Phillips et al." reference, delete "JMRL" and insert -- JMRI --; "Schatz et al." reference, delete "CIS" and insert -- CJS --; "Troussier, B. et al." reference, delete "30" and insert -- 20 --; and "Vorwerck et al." reference, delete "in" and insert -- im --.

Column 5,
Line 6, delete "$58a$" and insert -- $58\ a$ --.

Column 7,
Line 56, delete "$58a$" and insert -- $58\ a$ --.
Line 67, delete "a vascular" and insert -- avascular --.

Column 9,
Line 24, delete "$55a$" and insert -- $55\ a$ --.

Column 10,
Line 28, delete "$104a$" and insert -- $104\ a$ --.
Line 55, delete "$104a$" and insert -- $104\ a$ --.

Column 11,
Line 32, delete "will" and insert -- wall --.

UNITED STATES PATENT AND TRADEMARK OFFICE
CERTIFICATE OF CORRECTION

PATENT NO. : 6,695,839 B2
DATED : February 24, 2004
INVENTOR(S) : Hugh R. Sharkey and Gary S. Fanton It is certified that error appears in the above-identified patent and that said Letters Patent is hereby corrected as shown below:

<u>Column 12,</u>
Line 4, delete "distal" and insert -- disposed --.
Line 12, after "claim 2" insert -- , --.
Line 28, delete "whim" insert -- when --.

Signed and Sealed this

Twelfth Day of April, 2005

JON W. DUDAS
*Director of the United States Patent and Trademark Office*